(12) United States Patent
Wu et al.

(10) Patent No.: US 9,113,650 B2
(45) Date of Patent: Aug. 25, 2015

(54) PECTIC ENZYME TREATED PECTIN, METHOD OF PRODUCING THE SAME AND APPLICATION THEREOF

(75) Inventors: Ming-Chang Wu, Pingtung (TW); Yuh-Tai Wang, Taipei (TW); Ping-Hsiu Huang, Taichung (TW)

(73) Assignee: NATIONAL PINGTUNG UNIVERSITY OF SCIENCE AND TECHNOLOGY, Neipu (TW)

( * ) Notice: Subject to any disclaimer, the term of this patent is extended or adjusted under 35 U.S.C. 154(b) by 436 days.

(21) Appl. No.: 13/490,065

(22) Filed: Jun. 6, 2012

(65) Prior Publication Data

US 2013/0123211 A1    May 16, 2013

(30) Foreign Application Priority Data

Nov. 10, 2011    (TW) .............................. 100141068 A

(51) Int. Cl.

| | |
|---|---|
| *A61K 31/70* | (2006.01) |
| *A23L 1/0524* | (2006.01) |
| *C12P 19/04* | (2006.01) |
| *A23D 7/005* | (2006.01) |
| *C11B 5/00* | (2006.01) |
| *A61K 31/732* | (2006.01) |

(52) U.S. Cl.
CPC ............. *A23L 1/0524* (2013.01); *A23D 7/0053* (2013.01); *A61K 31/732* (2013.01); *C11B 5/0021* (2013.01); *C12P 19/04* (2013.01); *C12Y 301/01011* (2013.01); *C12Y 302/01015* (2013.01); *C12Y 402/0201* (2013.01)

(58) Field of Classification Search
CPC ..... A23L 1/0524; C12P 19/04; A61K 31/732; C12Y 402/0201; C12Y 301/01011
See application file for complete search history.

(56) References Cited

U.S. PATENT DOCUMENTS 7,491,708 B1    2/2009 Platt

FOREIGN PATENT DOCUMENTS

| JP | 200624043 | 7/2006 |
|---|---|---|
| TW | 200624043 | 7/2006 |

OTHER PUBLICATIONS

Kiss et al., "Kinetic Study on Hydrolysis of Various Pectins by Aspergillus Niger Polygalacturonase", Hungarian Journal of Industrial Chemistry VESPREM, vol. 36 (1-2), pp. 55-58 (2008).*
Huang et al, "Antioxidant Activity and Emulsion-Stabilizing Effect of Pectin Enzyme Treated Pectin in Soy Isolate-Stabilized Oil/Water Emulsion", Journal of Agricultural and Food Chemistry, vol. 59 (2011), pp. 9623-9628.*
Crinnion, Walter, Is Modified Citrus Pectin an Effective Mobilizer of Heavy Metals in Humans?, Alternative Medicine Review vol. 13, No. 4 2008.
Eliaz, et al., The Effect of Modified Citrus Pectin on Urinary Excretion of Toxic Elements, Published online Jul. 11, 2006 in Wiley InterScience (www.interscience.wiley.com) DOI: 10.1002/ptr.1953.
Funami, et al., Effects of the proteinaceous moiety on the emulsifying properties of sugar beet pectin, Food Hydrocolloids 21 (2007) 1319-1329.
Guess, et al., Modified citrus pectin (MCP) increases the prostate-specific antigen doubling time in men with prostate cancer: a phase II pilot study, Prostate Cancer and Prostatic Diseases (2003) 6, 301-304, 2003 Nature Publishing Group.
Hayashi, et al., Effects of Daily Oral Administration of Quercetin Chalcone and Modified Citrus Pectin on Implanted Colon-25 Tumor Growth in Balb-c Mice, Alternative Medicine Review, vol. 5, No. 6, 2000.
Huang, et al., The uptake of oligogalacturonide and its effect on growth inhibition, lactate dehydrogenase activity and galactin-3 release of human cancer cells, Food Chemistry (2012), doi:10.1016/j.foodchem.2011.12.037.
Jackson, et al., Pectin induces apoptosis in human prostate cancer cells: correlation of apoptotic function with pectin structure, Glycobiology vol. 17 No. 8 pp. 805-819, 2007.
Kidd, Parris, A New Approach to Metastatic Cancer Prevention: Modified Citrus Pectin (MCP), A Unique Pectin that Blocks Cell Surface Lectins, Alternative Medicine Review, vol. 1, No. 1, 1996.
Liu, et al., Inhibitory effect of modified citrus pectin on liver metastases in a mouse colon cancer model, *World J Gastroenterol*, Dec. 28, 2008; 14(48): 7386-7391, *World Journal of Gastroenterology* ISSN 1007-9327.
Lutz, et al., On the confocal images and the rheology of whey protein isolated and modified pectins associated complex, Colloids and Surfaces B: Biointerfaces 69 (2009) 43-50.
Nangia-Makker, et al., Inhibition of Human Cancer Cell Growth and Metastasis in Nude Mice by Oral Intake of Modified Citrus Pectin, Journal of the National Cancer Institute, vol. 94, No. 24, Dec. 18, 2002.
Rediguieri, et al., Thermodynamic Incompatibility and Complex Formation in Pectin/Caseinate Mixtures, Biomacromolecules 2007, 8, 3345-3354.
Veldman, et al., Dietary pectin influences fibrin network structure in hypercholesterolaemic subjects, Thrombosis Research, vol. 86, No. 3, pp. 183-196, 1997.

* cited by examiner

*Primary Examiner* — Elli Peselev
(74) *Attorney, Agent, or Firm* — Michael A. Glenn; Perkins Coie LLP

(57) ABSTRACT

A pectic enzyme treated pectin (PET-pectin) and a method of producing the same are disclosed. Citrus pectin solution is subjected to an enzymatic hydrolysis by using a mixed pectinase solution under an acidic condition, so as to obtain PET-pectin that is completely hydrolyzed. The PET-pectin has several biological functions, including stability of emulsification, anti-oxidation and inhibition of cancer cell growth, thereby being applied on food emulsion stabilizers, food antioxidants and compositions for inhibiting cancer cell growth and so on.

6 Claims, 3 Drawing Sheets

PECTIC ENZYME TREATED PECTIN, METHOD OF PRODUCING THE SAME AND APPLICATION THEREOF

RELATED APPLICATIONS

This application claims priority to Taiwan Application Serial Number 100141068, filed on Nov. 10, 2011, which is herein incorporated by reference.

BACKGROUND

1. Field of Invention

The present invention relates to a pectic enzyme treated pectin (PET-pectin) and a method of producing the same. More particularly, the present invention relates to a PET-pectin with biological functions, including stability of emulsification, anti-oxidation and inhibition of cancer cell growth, a method of producing the same and application thereof.

2. Description of Related Art

After the storms of illegal addition of plasticizers in foods, the safety of food additives are concerned more. According to Article 3 of Act of Governing Food Sanitation in Taiwan, the term "food additives" shall mean materials that are added to or brought into contact with foods in the course of manufacturing, processing, preparation, packaging, transportation and storage of foods for the purpose of coloring, seasoning, preserving, bleaching, emulsifying, flavoring, stabilizing quality, enhancing fermentation, increasing viscosity, enriching nutritional value, preventing oxidation or otherwise. Currently, the allowed food additives are generally divided into two categories: natural and chemically synthetic. Moreover, the food additive is not normally consumed as a food by itself.

Pectin is one of the natural food additives widely used in food additives. Pectin is one of polysaccharides commonly found in the middle lamella of the cell walls in higher plants for bounding cells together, and it is second only to cellulose in annual production. Pectin is a polymer consisting mainly of esterified D-galacturonic acid resides in an alpha ($\alpha$)-1→4 glycoside linkage. Furthermore, pectin is a legal and natural food additive for the purpose of increasing viscosity and adjusting the sweetness without legal restrictions related to its usage.

Typically, the conventional modified pectin is made through chemical reactions by adding chemical reagents such as acids or alkalis. However, the chemical reagents may remain in the modified pectin. Moreover, the drainage of the recovered chemical reagents may pollute the environment.

There is, however, a continuous need for naturally and non-chemically modified pectin and a method of producing the same, for overcoming all issues of chemically modified pectin and exploring more applications of the modified pectin.

SUMMARY

A method of producing pectic enzyme treated pectin (PET-pectin) is provided. The method comprises to subject Citrus pectin solution to an enzymatic hydrolysis by using a mixed pectinase solution, so as to obtain completely hydrolyzed pectin.

Moreover, a PET-pectin derived from pectin hydrolysate that is obtained by using the aforementioned method is provided.

Furthermore, a food emulsion stabilizer comprising the aforementioned PET-pectin as an active component of emulsification stability is provided.

Likewise, a food antioxidant comprising the aforementioned PET-pectin as an active component of antioxidation is provided.

In addition, a composition for inhibiting growth of cancer cells comprising the aforementioned PET-pectin as an active component of inhibition of growth of cancer cells is provided.

Accordingly, the invention provides a method of producing PET-pectin. In an embodiment, Citrus pectin solution is subjected to an enzymatic hydrolysis by using a mixed pectinase solution under an acidic condition of pH 4.0 and a temperature of 45 degree Celsius (° C.) to 65° C. for 1 hour to 72 hours, so as to obtain pectin hydrolysate. The Citrus pectin solution has a pectin concentration of 1 percent by volume to 3 percent by volume, the mixed pectinase solution comprises pectin methyl esterase (PME), polygalacturonase (PG) and pectin lyase (PL), and a volume ratio of the mixed pectinase solution to the Citrus pectin solution is 1:1000.

Next, the pectin hydrolysate is subjected to a thermal treatment under a temperature of 100° C. for 10 minutes, so as to terminate the enzymatic hydrolysis and obtain PET-pectin that is completely hydrolyzed. The PET-pectin has an averaged molecular weight of less than or equal to 1 kilodalton (kDa), an averaged degree of esterification (DE) of 11.6% and an averaged diameter of 2000 nanometers (nm).

Moreover, the invention further provides a PET-pectin derived from pectin hydrolysate that is obtained by using the aforementioned method.

Furthermore, the invention further provides a food emulsion stabilizer comprising the aforementioned PET-pectin as an active component of emulsification stability. The PET-pectin has 1.1 to 2.9 folds of an emulsification activity (EA) and 1.2 to 2.0 folds of an emulsification stability (ES) based on the EA and the ES of oil-in-water emulsion stabilized by a soybean isolated protein (SPI-stabilized O/W emulsion) calculated as one fold.

Likewise, the invention further provides a food antioxidant comprising the aforementioned PET-pectin as an active component of antioxidation. Trolox equivalent antioxidant capacity (TEAC) of the PET-pectin per one gram is equivalent to 4.3 mM trolox.

In addition, the invention further provides a composition for inhibiting growth of cancer cells comprising the aforementioned PET-pectin as an active component of inhibition of growth of cancer cells. The PET-pectin inhibits growth of cancer cells 3 percents to 60 percents.

In application of the PET-pectin and a method of producing the same, citrus pectin solution is subjected to the enzymatic hydrolysis by using the mixed pectinase solution. The PET-pectin is completely hydrolyzed and has several biological functions, including stability of emulsification, anti-oxidation and inhibition of cancer cell growth, thereby being applied on food emulsion stabilizers, food antioxidants and compositions for inhibiting cancer cell growth and so on.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
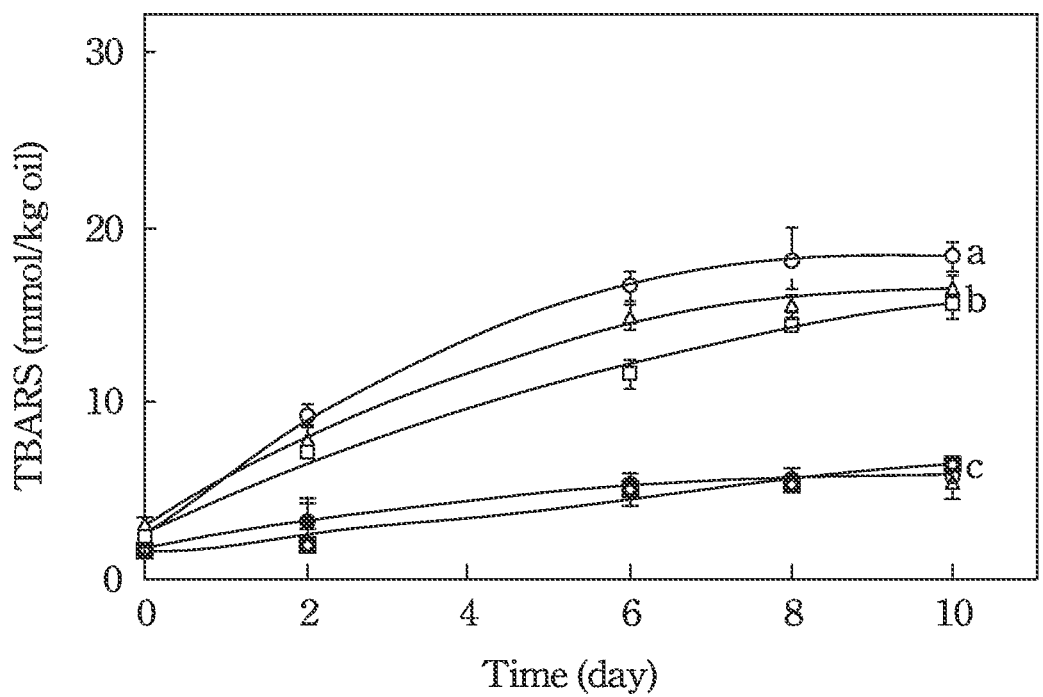
FIG. 1 shows a curve diagram with respect to oxidative stability of the O/W emulsion stabilized by the PET-pectin according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

As aforementioned, the present invention relates to a PET-pectin and a method of producing the same, in which Citrus pectin solution is subjected to an enzymatic hydrolysis by using a mixed pectinase solution under an acidic condition, so as to obtain completely hydrolyzed pectin.

Typically, the "Citrus pectin solution" as discussed hereinafter is referred to the pectin that is obtained by cutting Citrus peels and/or pulps into small pieces and then extracted by alkalis, acids or other conventional treatments. In considerations of lots of peel and/or pulp residues that are generated from juices, cans, jams and so on while citrus fruits are subjected to food processing, they are approximately 50% of the total mass of the Citrus fruit. Any disposal of incineration treatment of the remaining peel and/or pulp residues without concern after food processing will cause secondary pollutions of water, soil, gas and so on. According to past studies, Citrus fruit peels and/or pulps contain rich functional ingredients. If such discarded peels and/or pulps residues are reused, it will be environmentally friendly and create new value of the discarded peels and/or pulps.

Suitable Citrus fruits can include but be not limited to orange, lemon, grapefruit and so on. In an example, the Citrus pectin may be prepared to a pectin solution of 1 percent to 3 percents by volume. In another example, the concentration of the Citrus pectin solution may be 1 percent by volume.

In an embodiment, the Citrus pectin solution can be subjected to an enzymatic hydrolysis by using a mixed pectinase solution, so as to obtain c PET-pectin that is completely hydrolyzed. In an example, the mixed pectinase solution can be added into the Citrus pectin solution and an enzymatic hydrolysis is then performed under an acidic condition of pH 4.0 and a temperature of 45 degree Celsius (° C.) to 65° C. for 1 hour to 72 hours, so as to obtain pectin hydrolysate, in which a volume ratio of the mixed pectinase solution to the Citrus pectin solution is 1:1000. In another example, the enzymatic hydrolysis can be performed under 45° C. for 12 hours to 48 hours.

In those above examples, the mixed pectinase solution may comprise pectin methyl esterase (PME), polygalacturonase (PG) and pectin lyase (PL). In other examples, some commercial pectic enzymes can be used, for examples, Pectinex® (Novozymes, Switzerland), Pectinol (ROHM & HAAS Co., U.S.A.) or other commercial pectic enzyme produced by the method of Taiwanese Patent No. I337550. In addition, the pectic enzymes produced by microbes can further include other hydrolytic enzymes, for example, pectin esterase (PE), polygalacturonase (PG), pectin lyase (PL), cellulase and hemicellulase and the like. Many researches indicate that the pectic enzymes can be produced by bacteria, molds and yeasts, and exemplified by *Aspergillus niger, Penicillium dierckxii, Kluyveromyces maxianus, Penicillium griseoroseum, Rhizopus, Saccharomyces cerevisiae.*

And then, the pectin hydrolysate is subjected to a thermal treatment under a temperature of 100° C. for 10 minutes, so as to terminate the enzymatic hydrolysis and obtain PET-pectin that is completely hydrolyzed. In an example, the PET-pectin has an averaged molecular weight of less than or equal to 1 kilodalton (kDa), an averaged degree of esterification (DE) of 11.6% and an averaged diameter of 2000 nanometers (nm).

It is worth mentioned that, in another embodiment, the PET-pectin is further analyzed and evidenced that has several biological functions, including stability of emulsification, anti-oxidation and inhibition of cancer cell growth and so on.

In an example, the PET-pectin has 1.1 to 2.9 folds of an emulsification activity (EA) and 1.2 to 2.0 folds of an emulsification stability (ES) based on the EA and the ES of the SPI-stabilized O/W emulsion calculated as one fold. Therefore, the PET-pectin can be used as an active component of emulsification stability, for being applied on food emulsion stabilizers (or called cloudy agents) and replacing the conventional food emulsion stabilizers.

The food emulsion stabilizer, which is well known as a food additive, has gelling, thickening and emulsifying functions and is widely applied and commonly added into foods, for example, juices, jellies, jams, drinks, milks, bakery products, ice cream and so on. However, existing food emulsion stabilizers has some disadvantages such as few natural sources, high cost and only one emulsifying function. In one example of the natural emulsion stabilizers such as Palm oil, the Palm oil per kilogram is cost up to about 15 US dollars (USD) or about 400 New Taiwan Dollars (NTD). Moreover, the Palm oil is unstable and easy to be oxidized. In the past, some unscrupulous business people had even used one kilogram only 2 USD (or about 60 NTD) to 3 USD (or about 100 NTD) plasticizer to replace the Palm oil, resulting in substantial harm to human health. Comparison with the Palm oil, the PET-pectin of the invention per kilogram is only cost to about 6 USD to 7USD (or about 200 NTD), which is half of the cost of the Palm oil.

In another example, TEAC of the PET-pectin per one gram is equivalent to 4.3 mM trolox, for being as an active component of antioxidation and applied to a food antioxidant.

In a further example, the PET-pectin inhibit growth of cancer cells 3 percents to 60 percents, for being as an active component of inhibition of growth of cancer cells and applied to a composition for inhibiting growth of cancer cells Thereinafter, various applications of the PET-pectin and the method of producing the same will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

Example 1

Preparation of Citrus PET-Pectin

This EXAMPLE was directed to prepare Citrus PET-pectin by using Citrus fruit peels and/or pulps.

In the beginning, the Citrus fruit peels and/or pulps were cut into small pieces and then extracted by alkalis, acids or other conventional treatments, thereby extracting pectin. The Citrus pectin was quantitatively determined and prepared to Citrus pectin solution of 1 percent by volume. Conventional methods, which were adopted to extract and quantitatively determine of Citrus pectin, should be familiar to those skilled in the art rather than being described in detail.

Next, 1 mL of a mixed pectinase solution including PME, PG and PL is added into 1000 mL of Citrus pectin solution, and an enzymatic hydrolysis is then performed under an acidic condition of pH 4.0 and a temperature of 45 degree Celsius (° C.) to 65° C. for 0, 1, 6, 12, 24, 48 or 72 hours, so as to obtain completely hydrolyzed pectin. The aforementioned mixed pectinase solution may be commercial pectic enzymes, for example, including 50.6 U/mL of PME, 22.4 U/mL of PG and 133.5 U/mL of PL. The examples of commercial pectic enzymes may be Pectinex® (Novozymes, Switzerland) or other commercial pectic enzyme produced by the method of Taiwanese Patent No. I337550.

After performing the enzymatic hydrolysis, the aforementioned reactant was out into a boiling water bath for 10 minutes, so as to inactivate those enzymes. The reactant was then cooled and subjected to reduced-pressure concentration step and vacuum freeze-drying step, so as to obtain PET-pectin powder. Averaged molecular weight and averaged degree of esterification (DE) of the PET-pectin were listed in Table 1. The details of the reduced-pressure concentration step, the vacuum freeze-drying step, the averaged molecular weight and the averaged degree were well known to those skilled in the art rather than being recited in detail.

TABLE 1

|  | Averaged degree of esterification (DE; %) | Averaged molecular weight (kDa) |
|---|---|---|
| Pectin | 60.0 | 353 |
| Pectic enzyme treated pectin | 11.6 | 1 |

Example 2

Evaluation of Emulsification Activity and Emulsification Stability of PET-Pectin 1. Assessment of Emulsification Activity (EA)

This EXAMPLE was related to assess EA of Citrus PET-pectin of EXAMPLE 1 by using oil-in-water (O/W) emulsion stabilized by soy protein isolate (SPI-stabilized O/W emulsion).

The SPI-stabilized O/W emulsion of this EXAMPLE included 20% (v/v) of soybean oil and 1% (v/v) of SPI. The SPI-stabilized O/W emulsion of the control group was added with 1-2% of pectin. The SPI-stabilized O/W emulsion of the experiment group was added with 1-2% of pectin and/or 1-2% of PET-pectin. The compositions of the SPI-stabilized O/W emulsion of the control group and the experiment group were listed in TABLE 2.

Next, the SPI-stabilized O/W emulsion that included pectin and/or PET-pectin or not was emulsified in a tube by using a high-speed homogenizer for approximately 2 minutes under room temperature (e.g. 25° C. approximately), and then centrifuged at 4000 rpm for 20 minutes. EA was calculated according to the percentage of the height of the emulsified layer to the total height of each emulsion in the tube was measured and listed in the fifth column of TABLE 2, in which the higher value of the fifth column is referred to the better EA, and the maximum of the EA was 100%. In TABLE 2, data were expressed as the means±SEM, and the SEM (i.e. ±SEM) represented by the superscript texts "a", "b" and "c" posterior to the means respectively were a>b>c, in which the same superscript text between different groups (i.e. "a" and "a") was referred to the statically insignificant difference ($p>0.05$), and the different superscript texts between different groups (i.e. "b" and "c") were referred to the statically significant difference ($p<0.05$).

On the basis of the result of the fifth column of TABLE 2, the EA of the PET-pectin to emulsifying the SPI-stabilized O/W emulsion was approximately 37% to 98%.

2. Assessment of Emulsification Stability (ES)

This EXAMPLE was also related to assess ES of Citrus PET-pectin of EXAMPLE 1 by using the aforementioned SPI-stabilized O/W emulsion, and the SPI-stabilized O/W emulsion of this EXAMPLE was the same with the one listed in TABLE 2 rather than being repeated in detail.

Next, the SPI-stabilized O/W emulsion that included pectin and/or PET-pectin or not was emulsified in a tube by using a high-speed homogenizer for approximately 2 minutes under room temperature (e.g. 25° C. approximately), kept standing under 80° C. for 30 minutes, and then centrifuged at 4000 rpm for 20 minutes. ES was calculated according to the percentage of the height of the emulsified layer to the total height of each emulsion in the tube was measured and listed in the sixth column of TABLE 2, in which the higher value of the sixth column is referred to the better ES, and the maximum of the ES was 100%. In TABLE 2, data were expressed as the means±SEM, and the SEM (i.e. ±SEM) represented by the superscript texts "a", "b", "c", "d", "e" and "f" posterior to the means respectively were a>b>c>d>e>f, in which the same superscript text between different groups (i.e. "a" and "a") was referred to the statically insignificant difference ($p>0.05$), and the different superscript texts between different groups (i.e. "b" and "c") were referred to the statically significant difference ($p<0.05$).

According to the result of the sixth column of TABLE 2, the ES of the PET-pectin to emulsifying the SPI-stabilized O/W emulsion was approximately 35% to 78%.

In addition, the PET-pectin had 1.1 to 2.9 folds of EA and 1.2 to 2.0 folds of ES based on the EA and the ES of the SPI-stabilized O/W emulsion calculated as one fold. Therefore, the PET-pectin has the potential for being applied on the active component of food emulsion stabilizers and replacing the conventionally cloudy agents.

TABLE 2

| Soybean Oil (%) | SPI (%) | Pectin (%) | PET-Pectin (%) | Emulsification Activity (%) | Emulsification Stability (%) |
|---|---|---|---|---|---|
| 20 | 1 | 0 | 0 | $34.3 \pm 1.3^f$ | $39.7 \pm 0.5^e$ |
| 20 | 1 | 1 | 0 | $60.7 \pm 0.8^d$ | $50.1 \pm 1.8^c$ |
| 20 | 1 | 0 | 1 | $36.5 \pm 1.4^e$ | $49.3 \pm 1.4^c$ |
| 20 | 1 | 1 | 1 | $98.4 \pm 0.8^a$ | $78.2 \pm 1.0^a$ |
| 20 | 1 | 1 | 2 | $65.1 \pm 1.9^c$ | $62.0 \pm 1.6^b$ |
| 20 | 1 | 2 | 0 | $75.2 \pm 3.6^b$ | $35.8 \pm 2.2^f$ |
| 20 | 1 | 0 | 2 | $37.4 \pm 0.9^e$ | $46.1 \pm 1.2^d$ |

3. Assessment of Oxidative Stability

This EXAMPLE was related to assess oxidative stability of Citrus PET-pectin of EXAMPLE 1 by using the aforementioned SPI-stabilized O/W emulsion. Secondary oxidation products such as malondialdehyde (MDA) and so on, which were produced from lipid peroxidation of the O/W emulsion stored for a long period, could react with thiobarbituric acid (TBA) and generate red TBA-reactive substances (TBARS) under high temperature. The concentration of MDA was measured by detecting the light absorbance at 532 nm, thereby determine the lipid peroxidation level of a sample. The less absorbance is referred to the better inhibition of the lipid peroxidation (i.e. better oxidative stability) of the sample.

The SPI-stabilized O/W emulsion of this EXAMPLE was the same with the one listed in TABLE 2 rather than being repeated in detail.

In this EXAMPLE, each group listed in TABLE was stored at 50° C. for 10 days approximately. At every given storage time (e.g. 2 days), 100 μL aliquot of the stored emulsion was picked out, mixed with 900 μL of distilled water and 2 mL of 10% TBA reagent containing 15% (w/v) tricholoracetic acid and 0.375% (w/v) TBA, and then heated in a boiling water at 100° C. for 15 minutes. The reactant was cooled and centrifuged at 3000 rpm for 15 minutes for precipitation. The absorbance at 532 nm of 500 μL of the supernatant was measured for determining concentrations of MDA.

Reference is made to FIG. 1, which shows a curve diagram with respect to oxidative stability of the O/W emulsion stabilized by the PET-pectin according to an embodiment of the present invention, in which the horizontal axis is referred to the storage time (days), the vertical axis is referred to TBARS (mmol/kg oil), and each symbol of FIG. 1 corresponding to respective group is listed in TABLE 3. In TABLE 2, data are expressed as the means±SEM, and the SEM (i.e. ±SEM) represented by the superscript texts "a", "b" and "c" posterior to the means respectively are a>b>c, in which the same superscript text between different groups (i.e. "a" and "a") is referred to the statically insignificant difference (p>0.05), and the different superscript texts between different groups (i.e. "b" and "c") are referred to the statically significant difference ($p<0.05$).

TABLE 3

| | | Symbols | Soybean Oil (v/v %) | SPI (w/v %) | Pectin (%) | PET-Pectin (%) |
|---|---|---|---|---|---|---|
| Control Group | 1 | ○ | 20 | 1 | 0 | 0 |
| | 2 | Δ | 20 | 1 | 1 | 0 |
| | 3 | □ | 20 | 1 | 2 | 0 |
| Experiment Group | 1 | ● | 20 | 1 | 0 | 1 |
| | 2 | ■ | 20 | 1 | 0 | 2 |
| | 3 | ▲ | 20 | 1 | 1 | 1 |
| | 4 | ◇ | 20 | 1 | 1 | 2 |

Based on the result of FIG. 1, the experiment groups 1 to 4 (i.e. the curves corresponding to the symbols ●, ■, ▲ and ◇) added with PET-pectin have less TBARS of 5 mmol/kg oil to 7 mmol/kg oil approximately. It is evidenced that the PET-pectin provides the long-term storage of the O/W emulsion with better oxidative stability in comparison with the control groups 1 to 3 (i.e. the curves corresponding to the symbols ○, Δ and □).

Example 3

Evaluation of Anti-Oxidative Ability of PET-Pectin

1. Assessment of DPPH Radical Scavenging Activity 4 mL of sample solutions (i.e. pectin solution, PET-pectin solution, BHT solution or Vit. E solution listed in TABLE 2) and freshly prepared 1 mL of 0.2 mM DPPH were mixed well for 30 minutes. And then, the light absorbance of those mixtures at 517 nm was detected by the spectrophotometer, and their DPPH radical scavenging activities (%) were calculated according to the following formula (I), in which the lower light absorbance was referred to the stronger DPPH radical scavenging activity. Each data of TABLE 4 is referred to the mean of samples in triplicate and the result is listed in the third column of TABLE 4.

$$DPPH \text{ radical scavenging activity } (\%) = \left(1 - \frac{\text{absorbance of sample}}{\text{absorbance of control}}\right) \times 100\% \quad (I)$$

Depending on the result of the third column of TABLE 4, the PET-pectin has better DPPH radical scavenging activity than BHT (0.01 mg/mL and 0.10 mg/mL) and Vit. E (0.01 mg/mL) ($p<0.05$).

2. Assessment of Trolox Equivalent Antioxidant Capacity (TEAC)

1.5 mL of distilled water, 0.25 mL of [2,2'-azino-bis(3-ethyl benzothiazoline-6-sulphonic acid) (ABTS; 100 mM), 0.25 mL of 50M hydrogen peroxide ($H_2O_2$), and 0.25 mL of 4.4 unit/mL peroxidase. The ABTS could serve as the free radical source. After the mixture reacted in the dark for 12 to 16 hours and generated stably blue-green ABTS, followed by adding 0.25 mL of various concentrations of sample solutions (i.e. pectin solution, PET-pectin solution, BHT solution or Vit. E solution listed in TABLE 2) and reacting for 10 minutes. And then, the light absorbance of those mixtures at 734 nm was detected by the spectrophotometer, and the result was listed in TABLE 4. Each data of TABLE 4 was referred to the mean of samples in at least or more than triplicate. The TEAC was calculated according to 6-hydroxy-2,5,7,8-tetramethyl-chroman-2-carboxylic acid (Trolox, water-soluble Vit. E analogue; Sigma, St. Louis, Mo., U.S.A.) standard curve established by using different concentrations of trolox as a reference. The results of TEAC are shown in FIG. 2 and the fourth column of TABLE 4.

Figure 2:
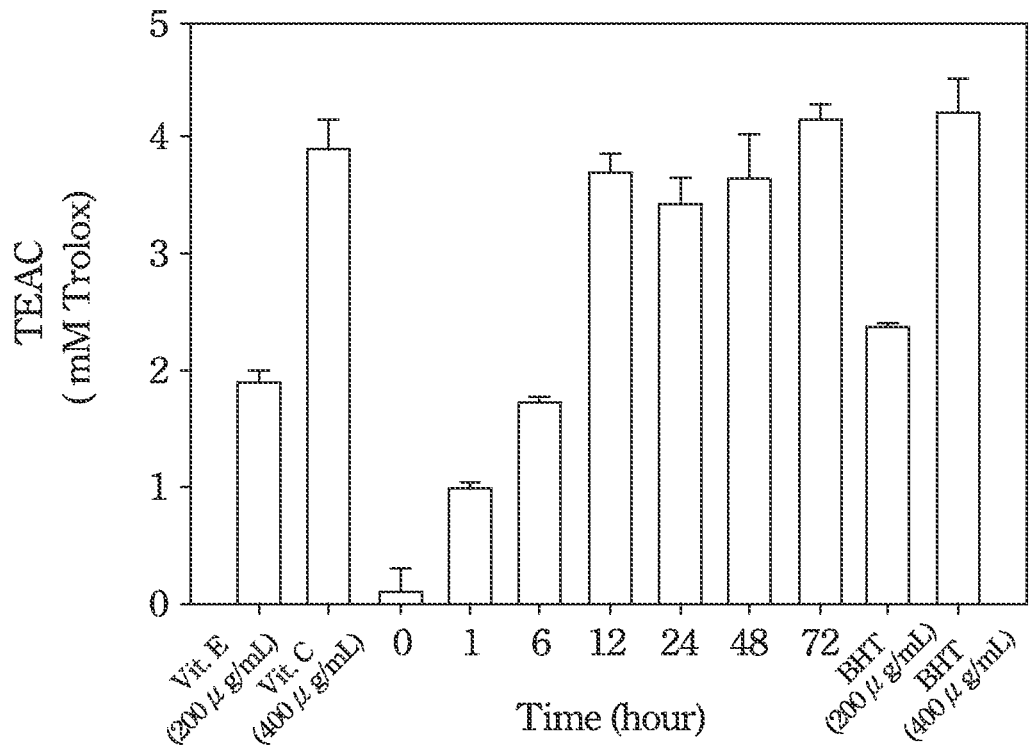
FIG. 2 shows a histogram with respect to TEAC of trolox incubated with the PET-pectin of various hydrolyzing time according to an embodiment of the present invention.

Reference is made to FIG. 2, which shows a histogram with respect to TEAC of trolox incubated with the PET-pectin of various hydrolyzing time according to an embodiment of the present invention, in which the horizontal axis is referred to the hydrolyzing time (hours), the vertical axis is referred to TEAC (mM trolox).

According to the result of FIG. 2, the PET-pectin with anti-oxidative activity can be obtained by hydrolysis for 1 hour to 72 hours; however, the one obtained by hydrolysis for 12 hour to 72 hours is preferable and better than 200 μg/mL of BHT and 200 μg/mL of Vit. E ($p<0.05$).

Reference is made to the fourth column of TABLE 4, which also shows similar results as FIG. 2. Depending on the result of the fourth column of TABLE 4, the PET-pectin has better TEAC than BHT (0.01 mg/mL and 0.10 mg/mL) and Vit. E (0.01 mg/mL) ($p<0.05$).

3. Assessment of Reducing Power

The reducing power of PET-pectin was determined by using the yield of Prussian blue [ferric ferrocyanide; $Fe_4(Fe(CN)_6)_3$] as the indicator. In brief, three-valent ferrous ion ($Fe^{3+}$) of red blood salt (potassium ferrocyanide; $K_3Fe(CN)_6$) was reduced to two-valent ferric ion ($Fe^{2+}$) of yellow blood salt ($K_4Fe(CN)_6$), followed by reacting yellow blood salt with the three-valent ferrous ion ($Fe^{3+}$) of ferric chloride ($FeCl_3$) to generate Prussian blue. And then, the light absorbance of Prussian blue at 700 nm was detected to evaluate the reducing power, in which the higher light absorbance was referred to the stronger reducing power.

This EXAMPLE could use the conventional method. The PET-pectin was prepared to various concentrations, each 20 μL aliquot of the sample solutions (i.e. pectin solution, PET-pectin solution, BHT solution or Vit. E solution listed in TABLE 2) was added with 50 μL of 0.2 M phosphate buffer (pH 6.6) containing 1% red blood salt [$K_3Fe(CN)_6$], incubated in water bath at 50° C. for 20 minutes and added with 50 μL of 10% trichloroacetic acid (TCA) solution. After being centrifuged at 1000 rpm for 10 minutes, 25 μL aliquot of the supernant was added with 65.9 μL of double deionized water and reacted with 9.1 μL of 0.1% ferric chloride ($FeCl_3$) solution. The absorbance at 700 nm is measured by the spectrophotometer and listed in the fifth column of TABLE 4, in which the higher light absorbance is referred to the stronger reducing power. Each data of TABLE 4 is referred to the mean of samples in at least or more than triplicate.

TABLE 4

| | concentration (mg/mL) | DPPH radical scavenging activity(%) | TEAC (mM Trolox) | Reducing Power ($OD_{700\,nm}$) |
|---|---|---|---|---|
| Pectin | 10.00 | $0.0 \pm 0.0^f$ | $0.0 \pm 0.0^d$ | $0.0 \pm 0.0^e$ |
| PET-pectin | 10.00 | $59.1 \pm 0.4^b$ | $4.3 \pm 0.1^a$ | $1.1 \pm 0.1^c$ |
| Butylated hydroxytoluene (BHT) | 0.01 | $5.2 \pm 0.4^e$ | $0.4 \pm 0.0^d$ | $0.5 \pm 0.0^d$ |
| | 0.10 | $49.2 \pm 2.9^c$ | $1.3 \pm 0.2^c$ | $1.7 \pm 0.1^b$ |
| α-tocopherol (Vit. E) | 0.01 | $46.1 \pm 0.4^d$ | $0.5 \pm 0.0^d$ | $0.6 \pm 0.0^d$ |
| | 0.10 | $96.8 \pm 0.5^a$ | $3.5 \pm 0.1^b$ | $2.5 \pm 0.0^a$ |

In TABLE 4, data are expressed as the means±SEM, and the SEM (i.e. ±SEM) represented by the superscript texts "a", "b", "c", "d", "e" and "f" posterior to the means respectively are a>b>c>d>e>f, in which the same superscript text between different groups (i.e. "a" and "a") is referred to the statically insignificant difference (p>0.05), and the different superscript texts between different groups (i.e. "b" and "c") are referred to the statically significant difference (p<0.05).

Based on the result of the fifth column of TABLE 4, the PET-pectin has better reducing power (TEAC) than BHT (0.01 mg/mL) and Vit. E (0.01 mg/mL) (p<0.05).

Example 4

In Vitro Evaluation of PET-Pectin for Inhibiting Growth of Cancer Cells

1. Cell Culture

This EXAMPLE was related to evaluate the effect of the PET-pectin to inhibit the growth rate of cancer cells, which was described as follows.

Human liver cancer cell line Hep-G2 C3A was purchased from the Food Industry Research and Development Institute (FIRDI), Bioresource Collection and Research Center (BCRC), Hsinchu, Taiwan under accession No.: BCRC 60177, which was derived from the same clone deposited at American Type Culture Collection (ATCC) under accession No.: ATCC CRL-10741). The lung cancer cell line A549 was also purchased from BCRC under accession No.: BCRC 60074, which was derived from the same clone deposited at ATCC under accession No.: ATCC CCL-185. The colorectal cancer cell line COLO-205 was also purchased from BCRC under accession No.: BCRC 60054, which was derived from the same clone deposited at ATCC under accession No.: ATCC CCL-222.

The cell lines Hep-G2 C3A was cultured in the minimum essential medium (MEM; Gibco® BRL, Grand Island, N.Y., U.S.A.) that contained 2 mM L-glutamine, Earle's balanced salt solution (Earle's BSS), 1.5 g/L of sodium bicarbonate, 0.1 mM non-essential amino acids, 1.0 mM of sodium pyruvate and 10% fetal bovine serum (FBS; Gibco® BRL, Rockville, Md., U.S.A.) or other functionally equivalent products thereof by using sterile cell culture techniques.

The lung cancer cell line A549 was cultured in the Ham's F12K medium (Gibco® BRL, Grand Island, N.Y., U.S.A.) that contained 2 mM L-glutamine, 1.5 g/L of sodium bicarbonate and 10% fetal bovine serum (FBS; Gibco® BRL, Rockville, Md., U.S.A.) or other functionally equivalent products thereof.

The colorectal cancer cell line COLO-205 was cultured in the RPMI 1640 medium (Gibco® BRL, Grand Island, N.Y., U.S.A.) that contained 2 mM L-glutamine, 1.5 g/L of sodium bicarbonate, 4.5 g/L of glucose, 10 mM HEPES, 1.0 mM of sodium pyruvate and 10% fetal bovine serum (FBS; Gibco® BRL, Rockville, Md., U.S.A.) or other functionally equivalent products thereof.

Those cells were incubated in an incubator (NUAIR NU4500, USA) with 5% $CO_2$ humidified atmosphere at 37° C., and changed with the fresh medium every two or three days.

When those cells reached about 90% confluence, the cells were gently washed in phosphate buffer saline (PBS) and subjected to trypsinization (1 mL of 0.25% trypsin-EDTA/plate), and the single cell solution was adjusted to cell density of $1 \times 10^6$ cells/mL, seeded into 96-well microplate with 100 μL cell solution per well (i.e. $1 \times 10^5$ cells/100 μL/well) and incubated with 5% $CO_2$ humidified atmosphere at 37° C.

After being cultured for 24 hours, each well was added with different concentrations (e.g. 200 μg/mL or 400 μg/mL) of PET-pectin (as experiment group) or equivalent volume of cell medium (as control group). After being co-cultured for 0 to 48 hours, the cells were harvested to calculate the cell viability by using 3-(4,5-dimethylthiazol-2-yl)-2,5-diphenyl tetrazolium bromide (MTT) assay or other conventional methods, so as to evaluate the effect of PET-pectin to inhibit the growth rate of the liver cancer cells, the lung cancer cells or the colorectal cancer cells in comparison with the cells of control group.

2. MTT Assay

In this EXAMPLE, MTT test could be performed according to the manufacturer's instructions. For example, 5 mg/mL methylthiazoletetrazolium (MTT; Sigma, St. Louis, Mo., USA) solution was firstly prepared by adding 5 mg MTT into 1 mL PBS. Next, each well (i.e. $1 \times 10^5$ cells/100 μL/well) of 96-well microplate was added with 10 μL MTT solution, incubated for 1 hours in the incubator (NUAIR NU4500, USA) in the dark with 5% $CO_2$ humidified atmosphere at 37° C., and then centrifuged for 10 minutes in a rotation speed of 1,000×g at 4° C. The supernatant was discarded and 100 μL of dimethyl sulfoxide (DMSO; Merck, Darmstadt, Germany) solution is added. The microplate was vibrated gently for 10 minutes. Absorbance at 550 nm ($OD_{550\,nm}$) of each well was detected by ELISA reader (Thermo, USA). By calculating cell viabilities of the control and experiment groups, the PET-pectin for inhibiting the growth rate of liver cancer cells, lung cancer cells or colorectal cancer cells could be evaluated. The results are shown in FIGS. 3A and 3C.

Figure 3A:
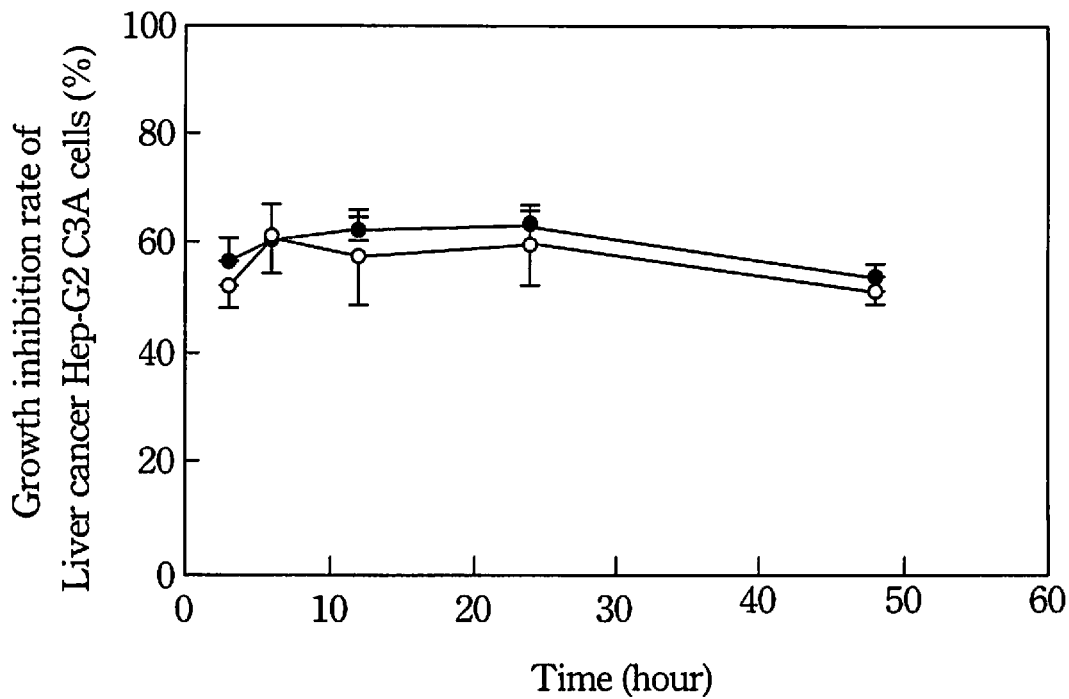
FIGS. 3A and 3C, show curve graphs of the growth inhibition rate of the liver cancer cell line Hep-G2 C3A (FIG. 3A), the lung cancer cell line A549 (FIG. 3B) and the colorectal cancer cell line COLO-205 (FIG. 3C) through the incubation with PET-pectin according to an embodiment of the present invention.
Figure 3B:
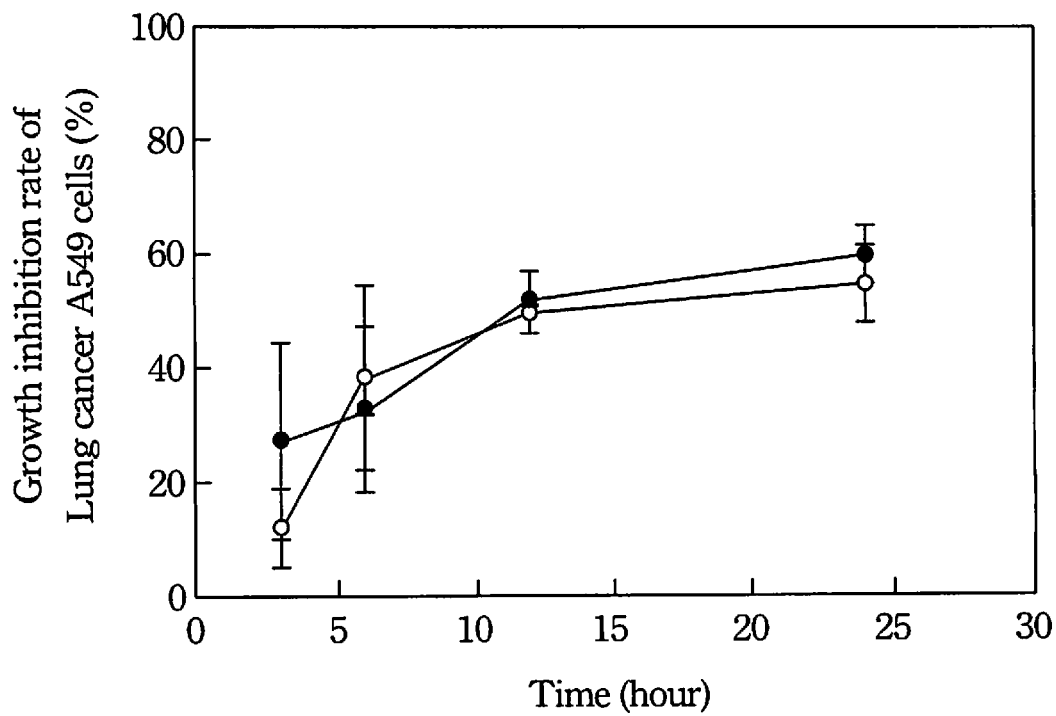
Figure 3C:
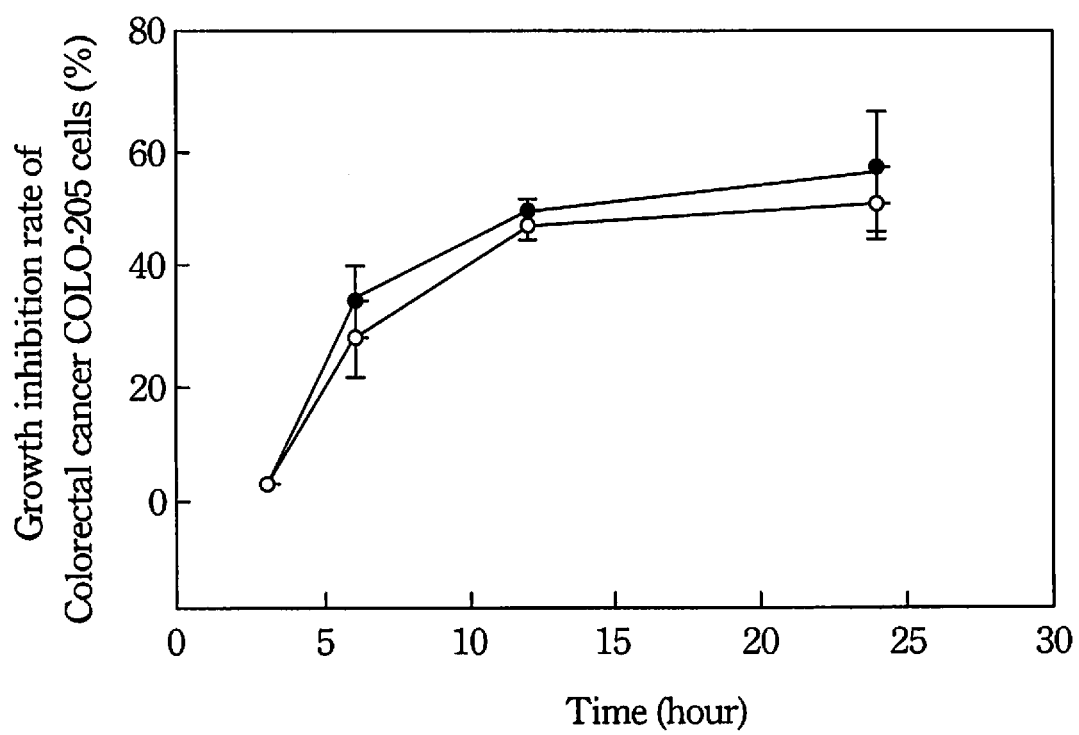

Reference is made to FIGS. 3A and 3C, which show curve graphs of the growth inhibition rate of the liver cancer cell line Hep-G2 C3A (FIG. 3A), the lung cancer cell line A549 (FIG. 3B) and the colorectal cancer cell line COLO-205 (FIG. 3C) through the incubation with PET-pectin according to an embodiment of the present invention, in which the horizontal axis of FIGS. 3A to 3C is referred to incubation time (hours), the vertical axis of FIGS. 3A to 3C is referred to the growth inhibition rate (%), the symbol "◯" is referred to the cell medium containing 200 μg/mL of PET-pectin, and the symbol "●" is referred to the cell medium containing 400 μg/mL of PET-pectin.

Based on the results of FIGS. 3A to 3C, as compared with the control cells that are incubated without the PET-pectin, the liver cancer cell line Hep-G2 C3A (FIG. 3A), the lung cancer cell line A549 (FIG. 3B) and the colorectal cancer cell line COLO-205 (FIG. 3C), all of which is incubated with the PET-pectin, have significantly increased growth inhibition rate, and the more PET-pectin results in the more growth inhibition rate. After being incubated with the PET-pectin at beginning several hours, the growth inhibition rate can be up to 300 percents approximately. Even after being incubated with the PET-pectin for 25 hours, the growth inhibition rate can reach 60 percents approximately. Therefore, the PET-pectin really has the potential for specifically inhibiting the growth of liver cancer cells, lung cancer cells or colorectal cancer cells.

As aforementioned, all measurements were carried out in triplicate. Values given in the tables and figures were expressed as means (standard deviation (SD) of triplicate measurements. Statistical analysis was accomplished using SAS Statistical Software, for Windows, version 9.1 (SAS, Cary, N.C.). The statistical significance of differences among means was evaluated using Duncan's multiple-range tests at a significant level of 0.05 ($p<0.05$).

In summary, the method of producing the PET-pectin of the present invention is involved to subject Citrus pectin solution to the enzymatic hydrolysis by using the mixed pectinase solution, so as to the PET-pectin, which is completely hydrolyzed and has several biological functions, including stability of emulsification, anti-oxidation and inhibition of cancer cell growth, thereby being applied on food emulsion stabilizers, food antioxidants and compositions for inhibiting cancer cell growth and so on. However, it is necessarily supplemented that, specific processes, specific analysis methods, specific assays, specific reaction conditions, specific test cells or specific apparatuses are exemplified for clarifying the PET-pectin of the present invention and the method of producing the same. However, as is understood by a person skilled in the art, other specific processes, other analysis methods, other assays, other reaction conditions, other test cells or other apparatuses can be also adopted in the PET-pectin of the present invention and the method of producing the same, rather than being limited thereto.

According to the embodiments of the present invention, the aforementioned PET-pectin and the method of producing the same advantageously use the mixed pectinase solution to enzymatically hydrolyze Citrus pectin solution, so as to obtain PET-pectin, which is completely hydrolyzed and has several biological functions, including stability of emulsification, anti-oxidation and inhibition of cancer cell growth, thereby being applied on food emulsion stabilizers, food antioxidants and compositions for inhibiting cancer cell growth and so on.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method of producing pectic enzyme treated pectin (PET-pectin), comprising:
    subjecting Citrus pectin solution to an enzymatic hydrolysis by using a mixed pectinase solution under an acidic condition of pH 4.0 and a temperature of 45 degree Celsius (° C.) for 12 hour to 48 hours, so as to obtain pectin hydrolysate, wherein the Citrus pectin solution has a pectin concentration of 1 percent by volume to 3 percent by volume, the mixed pectinase solution comprises pectin methyl esterase (PME), polygalacturonase (PG) and pectin lyase (PL), and a volume ratio of the mixed pectinase solution to the Citrus pectin solution is 1:1000; and
    subjecting the pectin hydrolysate to a thermal treatment under a temperature of 100° C. for 10 minutes, so as to terminate the enzymatic hydrolysis and obtain PET-pectin that is completely hydrolyzed,
    wherein the PET-pectin has an averaged molecular weight of less than or equal to 1 kilodalton (kDa), an averaged degree of esterification (DE) of 11.6% and an averaged diameter of 2000 nanometers (nm).

2. The method of producing PET-pectin of claim 1, wherein the Citrus pectin solution has the pectin concentration of 1 percent by volume.

3. The method of producing PET-pectin of claim 1, wherein the PET-pectin inhibit growth of cancer cells 3 percents to 60 percents.

4. The method of producing PET-pectin of claim 3, wherein the cancer cells are selected from the group consisting of liver cancer cells, lung cancer cells or colorectal cancer cells.

5. The method of producing PET-pectin of claim 1, wherein the PET-pectin has 1.1 to 2.9 folds of an emulsification activity and 1.2 to 2.0 folds of an emulsification stability based on the emulsification activity and the emulsification stability of oil-in-water emulsion stabilized by a soybean isolated protein calculated as one fold.

6. The method of producing PET-pectin of claim 1, wherein trolox equivalent antioxidant capacity (TEAC) of the PET-pectin per one gram is equivalent to 2.2 mM to 4.3 mM trolox.

* * * * *